(12) United States Patent
Kinouchi

(10) Patent No.: US 10,085,614 B2
(45) Date of Patent: Oct. 2, 2018

(54) OPTICAL COMMUNICATION SYSTEM AND ENDOSCOPE SYSTEM WITH CONNECTION STATE ABNORMALITY DETECTION

(71) Applicant: OLYMPUS CORPORATION, Tokyo (JP)

(72) Inventor: Hideaki Kinouchi, Musashino (JP)

(73) Assignee: OLYMPUS CORPORATION, Tokyo (JP)

( * ) Notice: Subject to any disclaimer, the term of this patent is extended or adjusted under 35 U.S.C. 154(b) by 23 days.

(21) Appl. No.: 15/379,159

(22) Filed: Dec. 14, 2016

(65) Prior Publication Data

US 2017/0095137 A1 Apr. 6, 2017

Related U.S. Application Data

(63) Continuation of application No. PCT/JP2015/056912, filed on Mar. 10, 2015.

(30) Foreign Application Priority Data

Sep. 1, 2014 (JP) .................................. 2014-177072

(51) Int. Cl.
  *A61B 1/04* (2006.01)
  *A61B 1/00* (2006.01)
  (Continued)

(52) U.S. Cl.
  CPC ...... *A61B 1/00013* (2013.01); *A61B 1/00006* (2013.01); *A61B 1/00009* (2013.01);
  (Continued)

(58) Field of Classification Search
  CPC ............ A61B 1/00006; A61B 1/00009; A61B 1/00013; A61B 1/00057; A61B 1/00117;
  (Continued)

(56) References Cited

U.S. PATENT DOCUMENTS

| 5,163,107 A * | 11/1992 | Garriss .................. G02B 6/325 385/124 |
| 6,353,692 B1 * | 3/2002 | Colbourne ........... G02B 6/3524 385/16 |

(Continued)

FOREIGN PATENT DOCUMENTS

| EP | 0 617 525 A1 | 9/1994 |
| JP | 5-176884 A | 7/1993 |

(Continued)

OTHER PUBLICATIONS

International Search Report dated Jun. 9, 2015 received in PCT/JP2015/056912.

(Continued)

*Primary Examiner* — John P Leubecker
(74) *Attorney, Agent, or Firm* — Scully, Scott, Murphy & Presser, P.C.

(57) ABSTRACT

A transmitting device includes: a first transmission unit; a second transmission unit having transmission lines each having a proximal end at which a transmitting-side connecting portion is provided; and a first switch for selecting a transmission line from the second transmission unit, to connect the selected transmission line to the first transmission unit. A receiving device includes: a third transmission unit having transmission lines each having a distal end at which a receiving-side connecting portion is provided; a fourth transmission unit; a second switch for selecting, from the third transmission unit, a transmission line including the receiving-side connecting portion optically connected to the transmitting-side connecting portion, to connect the selected transmission line to the fourth transmission unit; and a detection unit configured to detect whether a connection between the transmitting-side and receiving-side connecting (Continued)

portions is abnormal based on light amount of an optical signal transmitted through the fourth transmission unit.

6 Claims, 9 Drawing Sheets

(51) Int. Cl.

| | | |
|---|---|---|
| *G02B 6/35* | (2006.01) | |
| *G02B 23/24* | (2006.01) | |
| *H04B 10/075* | (2013.01) | |
| *G02B 6/38* | (2006.01) | |
| *G02B 23/26* | (2006.01) | |
| *H04B 10/079* | (2013.01) | |
| *H04N 7/18* | (2006.01) | |
| *A61B 1/045* | (2006.01) | |
| *A61B 1/05* | (2006.01) | |
| *H04N 7/22* | (2006.01) | |
| *H04N 5/225* | (2006.01) | |
| *A61B 1/06* | (2006.01) | |
| *A61B 1/07* | (2006.01) | |

(52) U.S. Cl.
CPC ...... *A61B 1/00055* (2013.01); *A61B 1/00057* (2013.01); *A61B 1/00105* (2013.01); *A61B 1/00117* (2013.01); *A61B 1/00126* (2013.01); *A61B 1/04* (2013.01); *A61B 1/045* (2013.01); *A61B 1/05* (2013.01); *G02B 6/35* (2013.01); *G02B 6/3895* (2013.01); *G02B 23/24* (2013.01); *G02B 23/2484* (2013.01); *G02B 23/26* (2013.01); *H04B 10/075* (2013.01); *H04B 10/0791* (2013.01); *H04N 7/183* (2013.01); *H04N 7/22* (2013.01); *A61B 1/0661* (2013.01); *A61B 1/07* (2013.01); *H04N 2005/2255* (2013.01)

(58) Field of Classification Search
CPC ........ A61B 1/00126; A61B 1/05; G02B 6/35; G02B 6/43; G02B 23/2484; H04B 10/75; H04B 10/0791; H04N 2005/2255; H04N 5/2252

See application file for complete search history.

(56) References Cited

U.S. PATENT DOCUMENTS

| | | | |
|---|---|---|---|
| 6,458,078 B1* | 10/2002 | Ludtke | A61B 1/00013 |
| | | | 348/E5.029 |
| 8,241,205 B2 | 8/2012 | Mori et al. | |
| 2002/0097462 A1* | 7/2002 | Koyano | H04B 10/032 |
| | | | 398/59 |
| 2007/0232860 A1* | 10/2007 | Kubo | A61B 1/00006 |
| | | | 600/160 |
| 2009/0058997 A1* | 3/2009 | Kato | H04N 7/183 |
| | | | 348/65 |
| 2009/0238556 A1* | 9/2009 | Yamada | H04J 14/02 |
| | | | 398/5 |
| 2010/0027943 A1* | 2/2010 | Armani | B01L 3/502715 |
| | | | 385/74 |
| 2012/0083655 A1* | 4/2012 | Kato | A61B 1/00055 |
| | | | 600/112 |
| 2013/0096380 A1* | 4/2013 | Matsuzawa | A61B 1/00013 |
| | | | 600/109 |
| 2013/0235175 A1* | 9/2013 | Kazama | H04N 7/18 |
| | | | 348/65 |
| 2014/0320619 A1* | 10/2014 | Nakamura | A61B 1/00036 |
| | | | 348/65 |
| 2016/0089001 A1* | 3/2016 | Hara | A61B 1/00013 |
| | | | 600/109 |

FOREIGN PATENT DOCUMENTS

| | | |
|---|---|---|
| JP | 8-125608 A | 5/1996 |
| JP | 10-261999 A | 9/1998 |
| JP | 2008-36356 A | 2/2008 |
| WO | WO 94/09575 A1 | 4/1994 |

OTHER PUBLICATIONS

Japanese Office Action dated Apr. 26, 2016 issued in 2016-502546.

* cited by examiner

FIG.6

| ROUTE | TRANSMISSION RATE OF OPTICAL SIGNAL (%) |
|---|---|
| R1 | 100 |
| R2 | 98 |
| R3 | 30 |

R1 ⟹ SELECTED

R2 ⟹ SELECTED

OPTICAL COMMUNICATION SYSTEM AND ENDOSCOPE SYSTEM WITH CONNECTION STATE ABNORMALITY DETECTION

CROSS REFERENCES TO RELATED APPLICATIONS

This application is a continuation of PCT international application Ser. No. PCT/JP2015/056912, filed on Mar. 10, 2015 which designates the United States, incorporated herein by reference, and which claims the benefit of priority from Japanese Patent Application No. 2014-177072, filed on Sep. 1, 2014, incorporated herein by reference.

BACKGROUND

1. Technical Field

The disclosure relates to an optical communication system an endoscope system for performing optical signal communication.

2. Related Art

Conventionally, endoscope systems have been used at the time of observing an internal organ of a subject such as a patient in the medical field. The endoscope system includes, for example: an endoscope having a distal end provided with an image sensor, having flexibility and elongate shape, and including an inserting portion to be inserted into a body cavity of the subject; and a processing device connected to the inserting portion via a cable and a connector (connecting portion), and adapted to apply image processing to an in-vivo image imaged by the image sensor and make a display device display the in-vivo image.

In recent years, development has been made on an image sensor having a large number of pixels and enabling observation of a clearer image, and use of such an image sensor having the large number of pixels in an endoscope is considered. Additionally, an inserting portion is demanded to have a smaller diameter, considering ease to introduce the endoscope into the subject. Furthermore, adopting an optical transmission system that transmits a signal by using laser light is also considered also in an endoscope system in order to transmit a signal having large capacity at a high speed between the image sensor and the processing device while achieving the small diameter of the inserting portion (refer to JP 2008-36356 A, for example).

SUMMARY

In some embodiments, an optical communication system includes: a transmitting device configured to transmit an optical signal, and a receiving device attachable to and detachable from the transmitting device and configured to receive the optical signal transmitted from the transmitting device. The transmitting device includes: a first optical transmission unit having a single optical transmission line to receive the optical signal; a second optical transmission unit having a plurality of optical transmission lines each having a proximal end at which a transmitting-side optical connecting portion is provided; and a first optical switch configured to select at least one optical transmission line from the second optical transmission unit, and to connect the at least one selected optical transmission line to the first optical transmission unit. The receiving device includes: a third optical transmission unit having a plurality of optical transmission lines each having a distal end at which a receiving-side optical connecting portion is provided, the receiving-side optical connecting portion being optically connectable to the transmitting-side optical connecting portion, and the third optical transmission unit being configured to transmit the optical signal received from the receiving-side optical connecting portion; a fourth optical transmission unit having a single optical transmission line to transmit the optical signal; a second optical switch configured to select, from the third optical transmission unit, an optical transmission line including the receiving-side optical connecting portion connected to the transmitting-side optical connecting portion of the at least one optical transmission line selected from the second optical transmission unit by the first optical switch, and to connect the selected optical transmission line to the fourth optical transmission unit; a control unit configured to control switching between the optical transmission lines connected to the first optical switch, and to control switching between the optical transmission lines connected to the second optical switch; and an abnormality detection unit configured to detect whether or not a connection state between the transmitting-side optical connecting portion and the receiving-side optical connecting portion is abnormal based on light amount information of the optical signal transmitted through the fourth optical transmission unit by way of the optical transmission lines selected in accordance with switching control of the first optical switch and the second optical switch by the control unit.

In some embodiments, an endoscope system includes an endoscopic device configured to be inserted into a subject to image an inside of the subject, and a processing device to and from which the endoscopic device is attachable and detachable. The endoscopic device includes: an imaging unit having a plurality of pixels arranged in a matrix form and configured to perform photoelectric conversion on light from an object irradiated with the light to generate an image signal; an optical signal conversion unit configured to convert the image signal to an optical signal; a first optical transmission unit having a single optical transmission line to receive the optical signal; a second optical transmission unit having a plurality of optical transmission lines each having a proximal end at which a transmitting-side optical connecting portion is provided; and a first optical switch configured to select at least one optical transmission line from the second optical transmission unit, and to connect the at least one selected optical transmission line to the first optical transmission unit. The processing device includes: a third optical transmission unit having a plurality of optical transmission lines each having a distal end at which a receiving-side optical connecting portion is provided, the receiving-side optical connecting portion being optically connectable to the transmitting-side optical connecting portion, and the third optical transmission unit being configured to transmit the optical signal received from the receiving-side optical connecting portion; a fourth optical transmission unit having a single optical transmission line; a second optical switch configured to select, from the third optical transmission unit, an optical transmission line including the receiving-side optical connecting portion connected to the transmitting-side optical connecting portion of the at least one optical transmission line selected from the second optical transmission unit by the first optical switch, and to connect the selected optical transmission line to the fourth optical transmission unit; a control unit configured to control switching between the optical transmission lines connected to the first optical switch, and to control switching between the optical transmission lines connected to the second optical switch; an abnormality detection unit configured to detect whether or not a connection state between the transmitting-side optical connecting portion and the receiving-side optical connecting portion is abnormal based on light amount information of the optical signal transmitted through the fourth optical transmission unit by way of the optical transmission lines selected in accordance with switching control of the first optical switch and the second optical switch by the control unit; and an image processing unit configured to process the image signal based on the optical signal transmitted through the fourth optical transmission unit.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 6 is an exemplary table illustrating respective routes transmission rates acquired by a determination unit illustrated in FIG. 5;

DETAILED DESCRIPTION

Reference will be made below to an endoscope system as modes for carrying out the present invention (hereinafter referred to as "embodiment(s)"). The present invention is not limited by the embodiments. The same reference signs are used to designate the same elements throughout the drawings.

First Embodiment

Figure 1:
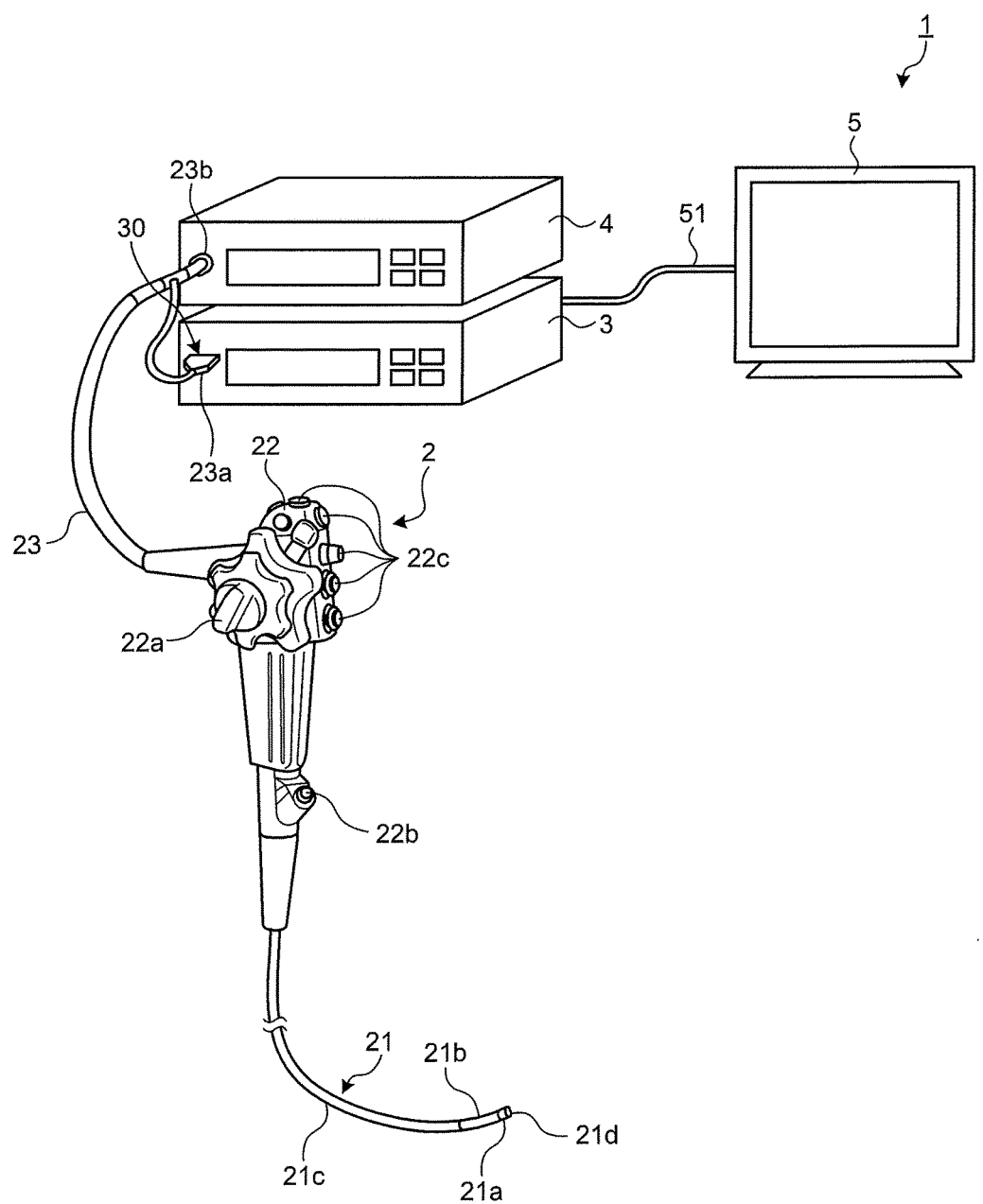
FIG. 1 is a schematic diagram illustrating an outline structure of an endoscope system according a first embodiment of the present invention.

FIG. 1 is a schematic diagram illustrating an outline structure of an endoscope system according a first embodiment of the present invention. As illustrated in FIG. 1, an endoscope system 1 according to the present embodiment includes: an endoscope 2 (scope) introduced into a subject and adapted to image inside of the subject and generate an image signal of the inside of the subject; a processing device 3 adapted to apply predetermined image processing to the image signal imaged by the endoscope 2 and also control each unit of the endoscope system 1; a light source device 4 adapted to generate illumination light of the endoscope 2; and a display device 5 adapted to perform image display of the image signal after application of the image processing by the processing device 3.

The endoscope 2 includes: an inserting portion 21 to be inserted into the subject; an operating unit 22 located on a proximal end portion side of the inserting portion 21 and gripped by an operator; and a flexible universal cord 23 extending from the operating unit 22.

The inserting portion 21 is implemented by using an illumination fiber (light guide cable), an electric cable, an optical cable (optical transmission line), and the like. The inserting portion 21 includes: a distal end portion 21a including an imaging unit incorporating an image sensor adapted to image the inside of the subject; a bendable portion 21b formed of a plurality of bending pieces; and a flexible tube portion 21c provided on a proximal end side of the bendable portion 21b and having flexibility. The distal end portion 21a includes: an illumination window adapted to emit illumination light to illuminate the inside of the subject via an illumination lens; an observation window adapted to image the inside of the subject; an opening portion 21d adapted to allow communication with a channel for a treatment tool, and a nozzle for air feeding/water feeding (not illustrated).

The operating unit 22 includes: a bending knob 22a adapted to bend the bendable portion 21b in a vertical direction and a horizontal direction; a treatment tool inserting portion 22b adapted to insert a treatment tool such as a biopsy forceps or a laser scalpel into the inside of the subject; the processing device 3; the light source device 4; and a plurality of switch units 22c adapted to operate peripheral devices such as an air feeding device, a water feeding device, and a gas feeding device. The treatment tool inserted from the treatment tool inserting portion 22b passes through the channel for the treatment tool provided inside and comes out from the opening portion 21d at a distal end of the inserting portion 21.

The universal cord 23 is formed by using an illumination fiber, an electric cable, or an optical cable. The universal cord 23 has a proximal end branched, and one branched end portion thereof is a connector 23a, and the other end portion is a connector 23b. The connector 23a is freely detached from a connector 30 of the processing device 3. The connector 23b is freely detached from the light source device 4. The universal cord 23 transmits the illumination light emitted from the light source device 4 to the distal end portion 21a via the connector 23b, operating unit 22, and the flexible tube portion 21c. The universal cord 23 transmits, to the processing device 3, an image signal imaged by the imaging unit provided at the distal end portion 21a.

The processing device 3 performs predetermined image processing on the image signal of the inside of the subject imaged by the imaging unit at the distal end portion 21a of the endoscope 2. The processing device 3 controls each unit of the endoscope system 1 based on various kinds of command signals transmitted from the switch unit 22c in the operating unit 22 of the endoscope 2 via the universal cord 23.

The light source device 4 is formed by using a light source that emits light, a condenser lens, and the like. The light source device 4 emits light from the light source under the control of the processing device 3, and supplies the light to the endoscope 2 connected via the connector 23b and the illumination fiber of the universal cord 23 as illumination light to the inside of the subject, namely, an object.

The display device 5 is formed by using a display such as a liquid crystal and an organic electro luminescence (EL). The display device 5 displays, via a video cable 51, various kinds of information including an image applied with the predetermined image processing by the processing device 3. Consequently, an operator can observe a desired position inside the subject body and determine a property thereof by operating the endoscope 2 while observing the image (in-vivo image) displayed by the display device 5.

Figure 2:
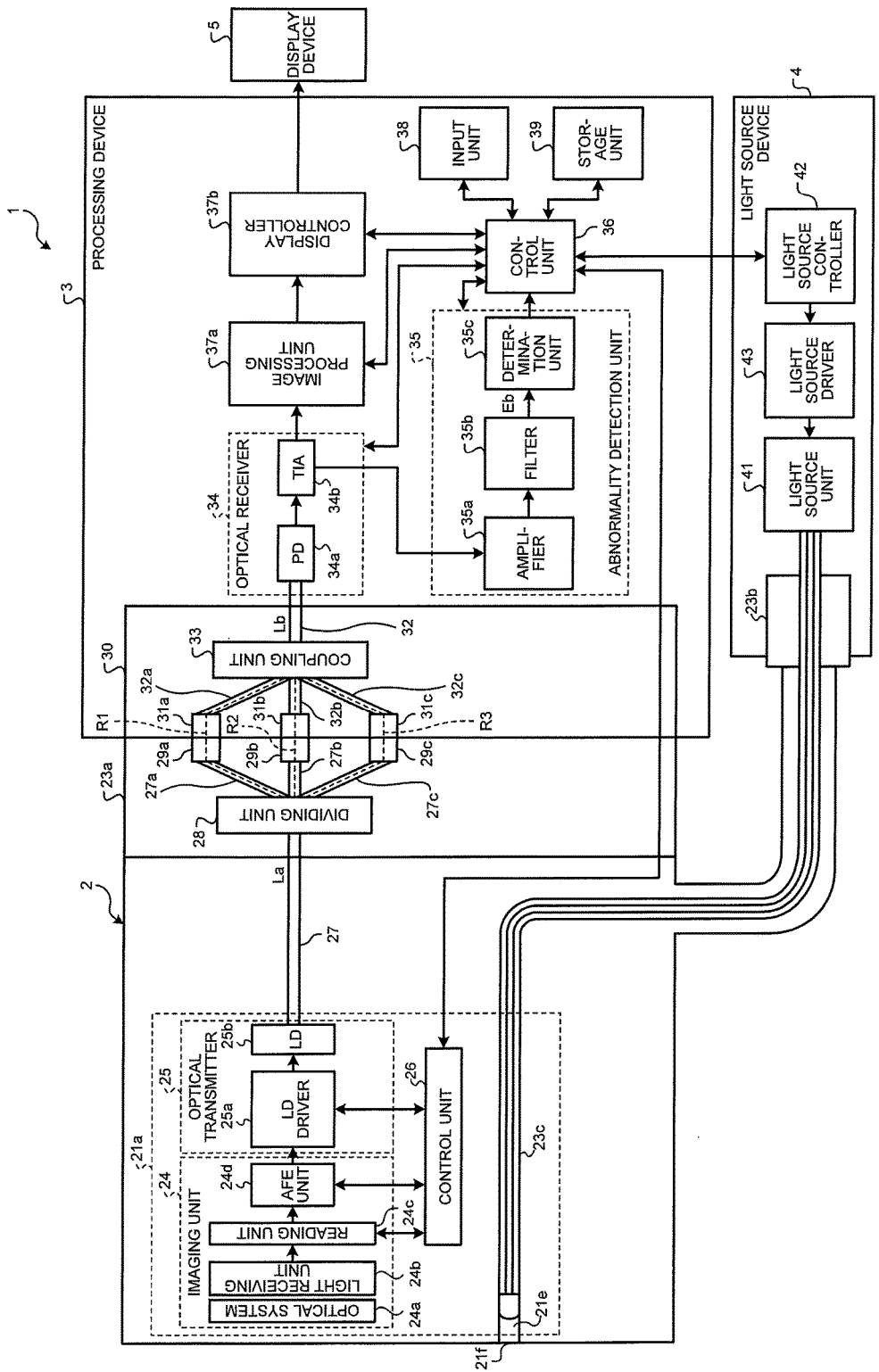
FIG. 2 is a block diagram schematically illustrating a configuration of the endoscope system illustrated in FIG. 1.

Next, configurations of the endoscope 2, processing device 3, and light source device 4 described in FIG. 1 will be described. FIG. 2 is a block diagram schematically illustrating a configuration of the endoscope system 1.

The endoscope 2 has the distal end portion 21a including an imaging unit 24, an optical transmitter 25 (optical signal conversion unit), and a control unit 26. Furthermore, in the distal end portion 21a, a distal end of a light guide cable 23c extending from the light source device 4 via the connector 23b is located. An illumination lens 21e is provided at the distal end of the light guide cable 23c. The light source device 4 emits the light to illuminate the object from an illumination window 21f at the distal end portion 21a of the inserting portion 21 via the light guide cable 23c.

The imaging unit 24 includes an optical system 24a, a light receiving unit 24b, a reading unit 24c, and an analog front end (AFE) unit 24d. The imaging unit 24 includes, for example, an image sensor such as a CCD image sensor or a CMOS image sensor.

The optical system 24a is formed by using one or a plurality of lenses, and has an optical zoom function to change a field angle and a focus function to change a focal point.

The light receiving unit 24b has a light receiving surface adapted to receive the light from the object irradiated with the light and arranged with a plurality of pixels in a matrix form in which the plurality of pixels photoelectrically converts the received light and generate image signals. The optical system 24a is disposed on the light receiving surface side of the light receiving unit 24b.

The reading unit 24c reads image signals generated by the plurality of pixels of the light receiving unit 24b. The image signal read by the reading unit 24c is an electric signal (analog).

The AFE unit 24d performs noise removal, A/D conversion, and the like for the electric signal of the image signal read by the reading unit 24c. The AFE unit 24d performs reduction of noise components included in the electric signal (analog), adjustment of amplification factor (gain) of the electric signal in order to keep an output level, and A/D conversion of the analog electric signal. The image signal generated by the imaging unit 24 is output to the processing device 3 via the optical transmitter 25, an optical cable 27 (first optical transmission unit), and the connector 23a.

The optical transmitter 25 converts, to an optical signal, an electric signal (digital) of the image signal output from the AFE unit 24d and outputs the converted optical signal to the optical cable 27. The optical transmitter 25 includes an LD driver 25a adapted to control drive of a laser diode (LD) 25b by supplying current to the LD 25b; and the LD 25b adapted to convert the electric signal of the image signal output from the AFE unit 24d to an optical signal (laser light).

The control unit 26 controls operation of the imaging unit 24 and the optical transmitter 25 in accordance with a control signal received from the processing device 3.

The optical cable 27 has a single optical transmission line to transmit the optical signal La obtained by conversion of the image signal by the LD 25b, to a dividing unit 28 at the connector 23a described later.

The endoscope 2 includes, in the connector 23a, the dividing unit 28, optical cables 27a to 27c (second optical transmission unit) formed of a plurality of optical cables, and optical connecting portions 29a to 29c (transmitting-side optical connecting portion).

The dividing unit 28 divides the optical signal La (first optical signal) of the image signal transmitted through the optical cable 27 into three and delivers the divided optical signals to the optical cables 27a to 27c, respectively. The optical cables 27a to 27c transmit the divided optical signals divided by the dividing unit 28 respectively. The optical connecting portions 29a to 29c are provided at proximal ends of the optical cables 27a to 27c, respectively. The proximal ends are output sides of the optical cables 27a to 27c. The optical connecting portions 29a to 29c are removably connectable to the corresponding optical connecting portions 31a to 31c on the processing device 3 side as an external member. Each of the optical connecting portions 29a to 29c includes: a GRIN lens connected to an optical fiber end surface of each of the corresponding optical cables 27a to 27c; and a cover glass adapted to cover a surface of the GRIN lens.

Next, the processing device 3 will be described. The processing device 3 includes a connector 30, an optical cable 32, an optical receiver 34, an abnormality detection unit 35, a control unit 36, an image processing unit 37a, a display controller 37b, an input unit 38, and a storage unit 39.

The connector 30 includes the optical connecting portions 31a to 31c (receiving-side optical connecting portions) and optical cables 32a to 32c (third optical transmission unit) formed of a plurality of optical cables, and a coupling unit 33.

The optical connecting portions 31a to 31c are provided at distal ends of the corresponding optical cables 32a to 32c, respectively. The distal ends are input sides of the optical cables 32a to 32c. The optical connecting portions 31a to 31c are removably connectable to the optical connecting portions 29a to 29c of the connector 23a of the endoscope 2 as an external member. Each of the optical connecting portions 31a to 31c includes a GRIN lens connected to an optical fiber end surface of each of the optical cables 32a to 32c described later, and a cover glass adapted to cover a surface of the GRIN lens. The optical connecting portion 31a and the optical connecting portion 29a on the endoscope 2 side have mutual connecting surfaces contacting each other, thereby connecting the optical cable 27a to the optical cable 32a. The optical connecting portion 31b and the optical connecting portion 29b have mutual connecting surfaces contacting each other, thereby connecting the optical cable 27b to the optical cable 32b. The optical connecting portion 31c and the optical connecting portion 29c have mutual connecting surfaces contacting each other, thereby connecting the optical cable 27c to the optical cable 32c.

The optical cables 32a to 32c transmit optical signals received in the corresponding respective optical connecting portions 31a to 31c. One of the divided optical signals divided in the dividing unit 28 is received in the coupling unit 33 described later via a route R1 passing through the optical cable 27a and the optical connecting portion 29a of the endoscope 2, optical connecting portion 31a connected to the optical connecting portion 29a, and optical cable 32a. Another one of the divided optical signals divided in the dividing unit 28 is received in the coupling unit 33 via a route R2 passing through the optical cable 27b, optical connecting portion 29b, optical connecting portion 31b, and optical cable 32b. Still another one of the divided optical signals divided in the dividing unit 28 is received in the coupling unit 33 via a route R3 passing through the optical cable 27c, optical connecting portion 29c, optical connecting portion 31c, and optical cable 32c.

The coupling unit 33 couples the three divided optical signals transmitted by the optical cables 32a to 32c to one optical signal and sends the coupled optical signal Lb (second optical signal) to the optical cable 32 (fourth optical transmission unit). The optical cable 32 has a single optical cable, and adapted to transmit the optical signal Lb received from the coupling unit 33 and deliver the same to the optical receiver 34.

The optical receiver 34 receives the optical signal Lb transmitted by the optical cable 32, converts the received optical signal Lb to an electric signal including light amount information of the optical signal Lb, and outputs the same to the image processing unit 37a and the abnormality detection unit 35. The converted electric signal is the electric signal including the light amount information of the optical signal Lb transmitted by the optical cable 32.

The optical receiver 34 includes: a PD 34a adapted to receive the optical signal Lb and convert the received optical signal Lb to an electric signal in accordance with the light amount thereof; and a transimpedance amplifier (TIA) 34b adapted to apply current/voltage conversion to the electric signal output from the PD 34a.

The abnormality detection unit 35 detects presence of abnormality in a connection state between the optical connecting portions 29a to 29c and the optical connecting portions 31a to 31c based on the light amount information of the optical signal Lb transmitted by the optical cable 32. The abnormality detection unit 35 includes: an amplifier 35a adapted to amplify the electric signal output from the TIA 34b; a filter 35b adapted to remove a DC component; and a determination unit 35c adapted to determine presence of abnormality in the connection state between the optical connecting portions 29a to 29c and the optical connecting portions 31a to 31c based on an electric signal Eb output from the filter 35b. The electric signal Eb is an electric signal including the light amount information in the optical signal Lb.

If the light amount of the optical signal Lb transmitted through the optical cable 32 is lower than a light amount (first light amount) that is large enough to preserve a specific level of transmission quality of the optical signal (allowing the processing device 3 to obtain images for observation, diagnosis, and procedure in the endoscope system), the determination unit 35c determines that a connection state between the optical connecting portions 29a to 29c and the optical connecting portions 31a to 31c is abnormal. The determination unit 35c determines presence of abnormality in the connection state between the optical connecting portions 29a to 29c and the optical connecting portions 31a to 31c based on the light amount information of the optical signal Lb included in the electric signal Eb output from the amplifier 35a and the filter 35b after conversion by the optical receiver 34. The abnormality detection unit 35 outputs a detection result to the control unit 36.

The illumination control unit 36 is formed by using a CPU or the like. The control unit 36 controls processing operation in each unit of the processing device 3. The control unit 36 controls operation of the processing device 3 by, for example, transferring command information and data to each element of the processing device 3. The control unit 36 is connected to the control unit 26 of the endoscope 2 and each element of the light source device 4 via cables, and controls operation of the imaging unit 24, optical transmitter 25, control unit 26, and light source device 4 as well.

The image processing unit 37a performs predetermined signal processing on an image signal (electric signal) output from the optical receiver 34, namely, an image signal generated by the imaging unit 24 under the control of the control unit 36. The image processing unit 37a performs, for the image signal, various kinds of image processing including optical black subtraction processing, gain adjustment processing, image signal synchronization processing, gamma correction processing, white balance (WB) processing, color matrix arithmetic processing, color reproduction processing, edge emphasis processing, and the like.

The display controller 37b generates, from the image signal processed by the image processing unit 37a, a display image signal to make the display device 5 perform display. The display image signal output to the display device 5 is, for example, a digital signal in a form of SDI, DVI, HDMI (registered trademarks), and the like. Furthermore, in the case where the abnormality detection unit 35 detects an abnormal connection state between the optical connecting portions 29a to 29c and the optical connecting portions 31a to 31c, the display controller 37b causes, under the control of the control unit 36, the display device 5 to display and output abnormal information indicating abnormality of the connection state between the optical connecting portions 29a to 29c and the optical connecting portions 31a to 31c.

The input unit 38 is implemented by an operation device such as a mouse, a keyboard, and a touch panel, and receives input of various kinds of information of the endoscope system 1. Specifically, the input unit 38 receives input of the various kinds of information such as subject information (e.g., ID, date of birth, name, etc.), identification information of the endoscope 2 (e.g., ID and examination item), and examination matters.

The storage unit 39 is implemented by a volatile memory or a non-volatile memory, and stores various kinds of programs in order to operate the processing device 3 and the light source device 4. The storage unit 39 temporarily records information being processed in the processing device 3. The storage unit 39 stores an image signal imaged by the imaging unit 24 and an image signal applied with the image processing by the image processing unit 37a. The storage unit 39 may also be formed by using a memory card and the like attached from the outside of the processing device 3.

Next, the light source device 4 will be described. The light source device 4 includes a light source unit 41, a light source controller 42, and a light source driver 43.

The light source unit 41 is formed by using, for example, a white light source formed of a white light LED and the like and an optical system such as a condenser lens.

The light source controller 42 controls light emitting operation of the light source unit 41 by controlling power supply by the light source driver 43 based on control by the control unit 36 of the processing device 3.

The light source driver 43 supplies predetermined power to the light source unit 41 under the control of the light source controller 42. Consequently, the light emitted from the light source unit 41 is made to illuminate the object from the illumination window 21f at the distal end portion 21a of the inserting portion 21 via the connector 23b and the light guide cable 23c inside the universal cord 23. The imaging unit 24 is disposed in the vicinity of the illumination window 21f.

Next, determination processing relative to the connection state between the optical connecting portions 29a to 29c and the optical connecting portions 31a to 31c by the determination unit 35c will be described. The optical signal Lb that is to be the base of determination in the determination unit 35c is the optical signal obtained by dividing an optical signal into three in the dividing unit 28 on the endoscope 2 side, transferring the three divided optical signals via the three routes R1 to R3, and then coupling the transmitted three divided optical signals to one in the coupling unit 33 on the processing device 3 side. The three routes R1 to R3 are formed of the optical cables 27a to 27c, optical connecting portions 29a to 29c, optical connecting portions 31a to 31c, and optical cables 32a to 32c. Furthermore, the electric signal Eb is the signal obtained by photoelectrically converting the optical signal Lb.

Figure 3:
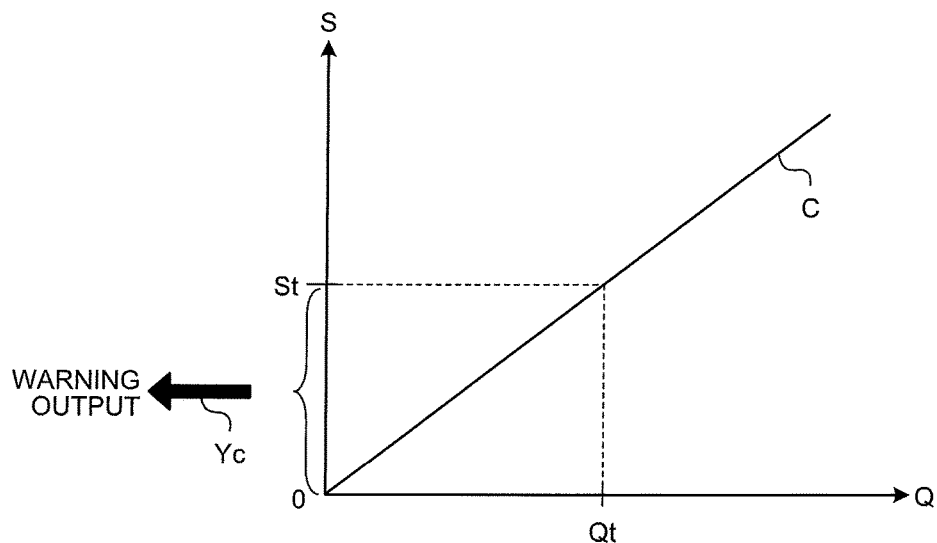
FIG. 3 is a diagram illustrating a relation between intensity of an electric signal output from a filter illustrated in FIG. 2 and a light amount of an optical signal output from a coupling unit.

FIG. 3 is a diagram illustrating a relation between intensity S of the electric signal Eb and a light amount Q of the optical signal Lb. As illustrated in FIG. 3, the intensity S of the electric signal Eb and the light amount Q of the optical signal Lb have a proportional relation represented by a straight line C, for example. This straight line C is reflected with various kinds of coefficients in the PD 34a, TIA 34b, amplifier 35a, and filter 35b. Therefore, there is a relation in which when the light amount Q of the optical signal Lb is reduced, the intensity S of the electric signal Eb output from the filter 35b is also reduced.

When abnormality occurs in the connection state of any one of the optical connecting portions 29a to 29c and the optical connecting portions 31a to 31c due to dirt, fog, or angle deviation at the connecting surfaces of the optical connecting portions 29a to 29c and the optical connecting portions 31a to 31c, the light amount of the optical signal to be transmitted is attenuated in a route that passes through the optical connecting portion where abnormality occurs, and then transmission failure occurs. Furthermore, when the route where abnormality occurs is increased, the light amount Q of the optical signal Lb obtained by coupling the optical signals transmitted via all of the routes R1 to R3 is also attenuated, and when the light amount Q of the optical signal Lb is lower than a predetermined light amount Qt, a specific level of transmission quality of the optical signal cannot be preserved. Therefore, in the case where the intensity S of the electric signal Eb output from the filter 35b is lower than intensity St corresponding to the light amount Qt, it can be said that this is the state in which abnormality occurs at any one of the optical connecting portions 29a to 29c and the optical connecting portions 31a to 31c due to dirt or fog at a portion of the connecting surface of the optical connecting portion where the light passes, or due to angle deviation relative to a course of the light at the optical connecting portion, and a specific level of transmission quality of the optical signal cannot be preserved.

Therefore, the determination unit 35c determines the abnormal connection state between the optical connecting portions 29a to 29c and the optical connecting portions 31a to 31c if the intensity S of the electric signal Eb output from the filter 35b is lower than the intensity St that is large enough to preserve the specific level of transmission quality of the optical signal. The intensity St as a criterion for the determination is preliminarily stored in the storage unit 39 and the like, and the determination unit 35c refers to the intensity St stored in the storage unit 39 and the like, makes comparison with the intensity S of the electric signal Eb received from the filter 35b, and determines whether or not the connection state between the optical connecting portions 29a to 29c and the optical connecting portions 31a to 31c is abnormal. The determination unit 35c determines that any one of the connection state between the optical connecting portions 29a to 29c and the optical connecting portions 31a to 31c is abnormal if the intensity S of the electric signal Eb received from the filter 35b is lower than the intensity St.

Upon receipt of a determination result of the abnormality detection unit 35, the display controller 37b causes, under the control of the control unit 36, the display device 5 to display and output a warning menu indicating that the connection state between the optical connecting portions 29a to 29c and the optical connecting portions 31a to 31c is abnormal (refer to arrow Yc in FIG. 3). For example, in the warning menu, not only indication of an abnormal connection state at the optical connecting portions but also indication of necessity of cleaning in order to remove dirt or the like from the connecting surfaces of the connectors 23a, 30 are displayed, thereby urging a user to clean the connecting surface. Since the user of the endoscope system 1 confirms the warning menu displayed on the display device 5, the user can quickly recognize connection abnormality between the optical connecting portions 29a to 29c and the optical connecting portions 31a to 31c, and clean the respective connecting surfaces of the optical connecting portions 29a to 29c and the optical connecting portions 31a to 31c. As a result, transmission failure of the optical signal can be solved in an early stage.

Additionally, if the intensity S of the electric signal Eb output from the filter 35b is equal to or higher than the intensity St that is large enough to preserve the specific level of transmission quality of the optical signal, the determination unit 35c determines that the connection state between the optical connecting portions 29a to 29c and the optical connecting portions 31a to 31c is normal. In this case, the control unit 36 causes the display device 5 to display a normal menu and the like indicating that: the connection state between the optical connecting portions 29a to 29c and the optical connecting portions 31a to 31c is normal; the specific level of transmission quality of the optical signal can be preserved; and endoscopic examination can be started and continued.

Thus, according to the first embodiment, presence of abnormality in the connection state between the optical connecting portions 29a to 29c and the optical connecting portions 31a to 31c is automatically detected and transmission failure of the optical signal can be solved in an early stage by detecting presence of abnormality in the connection state between the optical connecting portions 29a to 29c and the optical connecting portions 31a to 31c constituting the routes R1 to R3 based on the optical signal Lb obtained by dividing an optical signal into three in the dividing unit 28 on the endoscope 2 side, transmitting the divided optical signals via the three respective routes R1 to R3, and coupling the transmitted three divided optical signals to one in the coupling unit 33 on the processing device 3 side.

For example, in the endoscope system 1, the abnormality detection unit 35 executes abnormality detection processing in pre-operation inspection and confirms presence of abnormality in the connection state between the optical connecting portions 29a to 29c and the optical connecting portions 31a to 31c. Consequently, the endoscope 2 can be started to be used in a state that reliability of optical transmission is secured. Needless to say, in the endoscope system 1, the connection state between the optical connecting portions 29a to 29c and the optical connecting portions 31a to 31c may also be monitored by the abnormality detection unit 35 executing the abnormality detection processing as needed while in use. Furthermore, in the case where transmission failure of an optical signal occurs while using the endoscope system 1, the abnormality detection unit 35 executes the abnormality detection processing. Consequently, it can be determined whether the transmission failure of the optical signal is caused by dirt and the like on the connecting surfaces between the optical connecting portions 29a to 29c and the optical connecting portions 31a to 31c or caused by other elements.

Additionally, according to the first embodiment, the optical signal is transmitted by being divided into the plurality of routes R1 to R3. Therefore, even in the case where connection abnormality occurs in a part between the optical connecting portions 29a to 29c and the optical connecting portions 31a to 31c, the optical signal can be transmitted via a different route. For example, in the example of FIG. 2, the optical signal is transmitted by being dispersed in the three routes. In the example of FIG. 2, even in the case where abnormality occurs at any one of the routes R1 to R3, the light amount of the optical signal transmitted to the processing device 3 that is the receiving side only becomes ⅔, and a large loss of the light amount of the optical signal can be suppressed. Therefore, the optical signal can be transmitted even without cleaning the optical contact portion, and risk can be dispersed.

Figure 4:
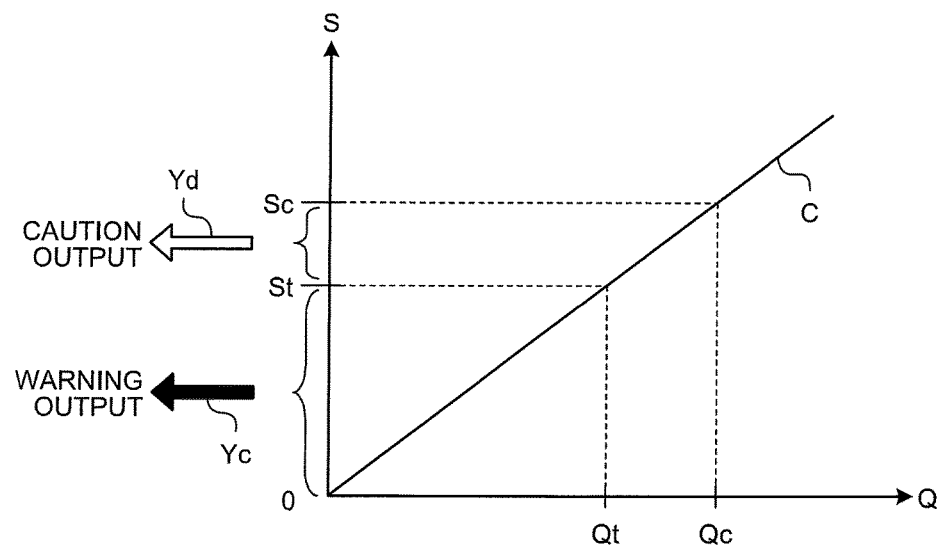
FIG. 4 is a diagram illustrating a relation between the intensity of the electric signal output from the filter illustrated in FIG. 2 and the light amount of the optical signal output from the coupling unit.

In the above explanation, the determination unit 35c compares the intensity S of the electric signal Eb with the intensity St of the electric signal corresponding to the light amount Qt of the optical signal that is large enough to preserve the specific level of transmission quality, but needless to say, not limited thereto. FIG. 4 is a diagram for explaining the abnormality determination processing in the determination unit 35c and also the diagram illustrating a relation between the intensity S of the electric signal Eb and the light amount Q of the optical signal Lb. As illustrated in FIG. 4, the determination unit 35c performs determination relative to a light amount Qc that is a light amount larger than the light amount Qt and requires caution for degradation of transmission quality of an optical signal (second light amount: corresponding to a light amount of an image that can be observed, diagnosed, and processed in the endoscope system 1 but has some noise), and in the case where the light amount Q of the optical signal Lb transmitted by the optical cable 32 is lower than the light amount Qc, the determination unit 35c determines that there may be possibility that the connection state between the optical connecting portions 29a to 29c and the optical connecting portions 31a to 31c becomes abnormal.

Specifically, in the case where the intensity S of the electric signal Eb is lower than intensity Sc corresponding to the light amount Qc of the optical signal Lb, the determination unit 35c determines that there may be possibility that the connection state between the optical connecting portions 29a to 29c and the optical connecting portions 31a to 31c becomes abnormal. Then, upon receipt of such a determination result, the display controller 37b causes, under the control of the control unit 36, the display device 5 to display and output a caution menu indicating that there may be possibility that the connection state between the optical connecting portions 29a to 29c and the optical connecting portions 31a to 31c becomes abnormal (refer to arrow Yd in FIG. 4). Consequently, the operator recognizes possibility that the connection state becomes abnormal, and can quickly handle the situation by performing examination and the like while paying attention to the connection state between the optical connecting portions even in the case where abnormality occurs in the connection state. Additionally, an actual attenuation rate may also be displayed together with warning and caution in the warning menu and the caution menu.

Second Embodiment

Figure 5:
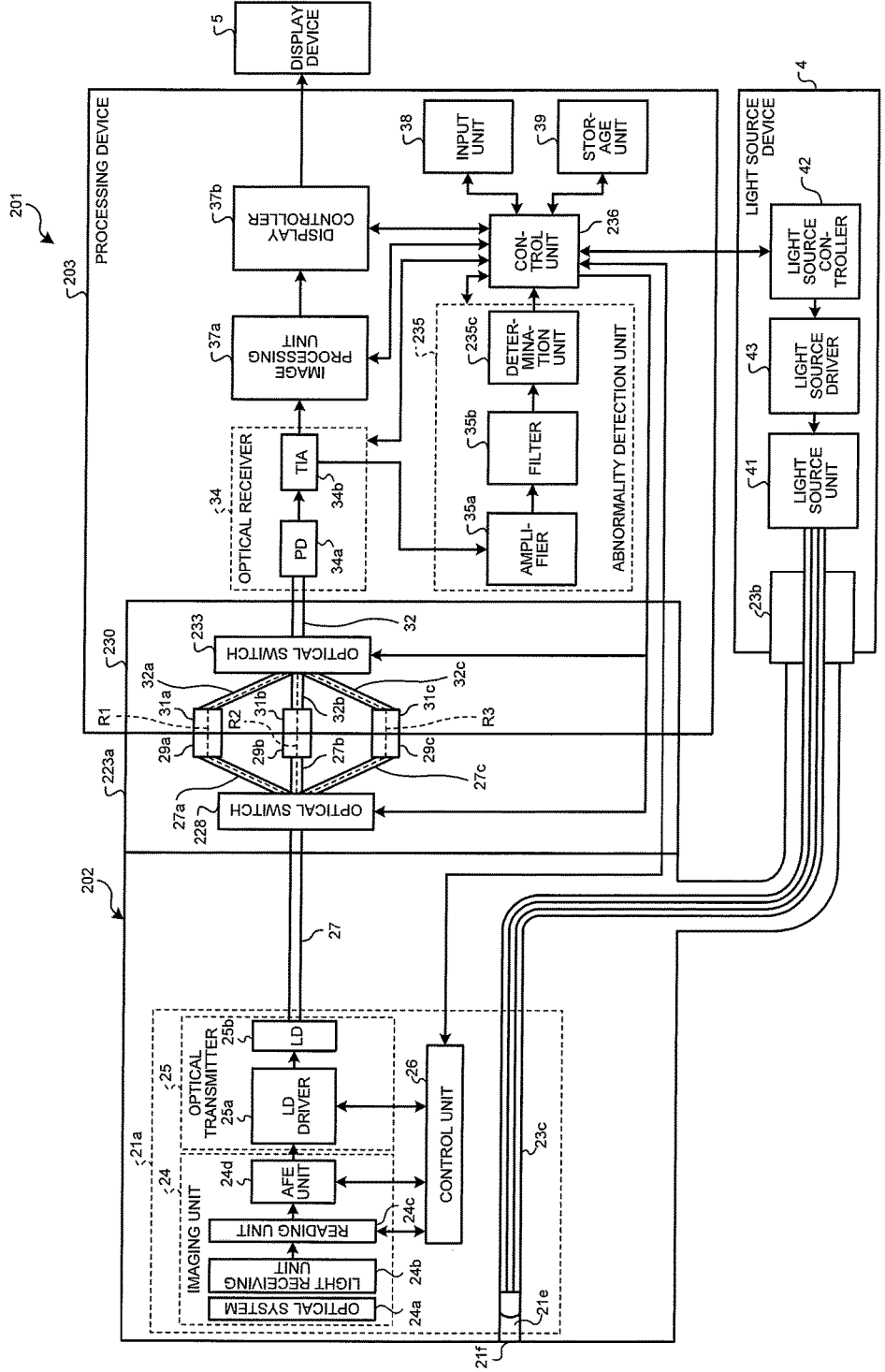
FIG. 5 is a block diagram schematically illustrating a configuration of an endoscope system according to a second embodiment.

Next, a second embodiment will be described. FIG. 5 is a block diagram schematically illustrating a configuration of an endoscope system according to the second embodiment.

As illustrated in FIG. 5, an endoscope system 201 according to the second embodiment includes: an endoscope 202 instead of an endoscope 2 in FIG. 2; and a processing device 203 instead of a processing device 3.

The endoscope 202 includes a connector 223a having an optical switch 228 instead of a dividing unit 28. The optical switch 228 selects at least one optical cable out of three optical cables 27a to 27c under the control of a control unit 236 of the processing device 203 described later, and connects the selected optical cable to an optical cable 27.

The processing device 203 includes: a connector 230 having an optical switch 233 instead of a coupling unit 33; an abnormality detection unit 235; and the control unit 236 (switch control unit).

Under the control of the control unit 236 described later, the optical switch 233 selects one or more of three optical cables 32a to 32c. The selected optical cable or cables are coupled to the corresponding one or more of the optical connecting portions 31a to 31c. The corresponding one or more of the optical connecting portions 31a to 31c are connected to the corresponding one or more of optical connecting portions 29a to 29c. One or more of the optical cables 27a to 27c selected by the optical switch 228 of the endoscope 202 are coupled to the corresponding one or more of the optical connecting portions 29a to 29c. The optical switch 233 connects the selected optical cable or cables to the optical cable 32.

If a light amount of an optical signal transmitted through the optical cable 32 is lower than a predetermined threshold (first light amount) that is large enough to preserve a specific level of transmission quality of the optical signal (allowing the processing device 203 to obtain images for observation, diagnosis, and procedure in the endoscope system 201), the abnormality detection unit 235 detects an abnormal connection state between one or more of the optical connecting portions 29a to 29c at a proximal end of the one or more of the optical cables 27a to 27c selected by the optical switch 228 and one or more of the optical connecting portions 31a to 31c at a distal end of the one or more of the optical cables 32a to 32c selected by the optical switch 233. The abnormality detection unit 235 includes a determination unit 235c instead of a determination unit 35c in FIG. 2. An electric signal output from a filter 35b is an electric signal including light amount information in the optical signal transmitted through the optical cable 32. Therefore, if intensity of the electric signal output from the filter 35b is lower than intensity corresponding to the above-described threshold of the light amount, the determination unit 235c determines that the connection state between one or more of the optical connecting portions 29a to 29c at the proximal end of the one or more of the optical cables 27a to 27c selected by the optical switch 228 and one or more of the optical connecting portions 31a to 31c at the distal end of the one or more of the optical cables 32a to 32c selected by the optical switch 233 is abnormal.

The control unit 236 has a function same as the control unit 36 and also controls the optical switch 228 and the optical switch 233 to control switching of optical cables to which the optical switch 228 and the optical switch 233 are connected respectively. The abnormality detection unit 235 detects presence of abnormality in the connection state between any one the optical connecting portions 29a to 29c and any one of the optical connecting portions 31a to 31c corresponding to any one of the routes R1 to R3 selected by the optical switch 228 and the optical switch 233 in accordance with switch control for the optical switch 228 and the optical switch 233 by the control unit 236. The control unit 236 controls the optical switch 228 and the optical switch 233 so as to select, out of the route R1 to R3, a route having no abnormal connection state detected by the abnormality detection unit 235 and corresponding to any one of the optical connecting portions 29a to 29c and any one of the optical connecting portions 31a to 31c.

Next, exemplary determination processing in the determination unit 235c relative to the connection state between the optical connecting portions 29a to 29c and the optical connecting portions 31a to 31c will be described. The determination unit 235c sequentially obtains, for each of the routes R1 to R3, a light amount of an optical signal transmitted via each of the routes R1 to R3, and obtains a transmission rate of the optical signal by making comparison with a light amount of an optical signal output from an optical transmitter 25 of the endoscope 202. Then, the determination unit 235c acquires a threshold of a transmission rate based on the light amount of the optical signal output from the optical transmitter 25 of the endoscope 202 and the above-described threshold of the light amount of the optical signal, and in the case where each of the obtained transmission rate is lower than the threshold of the transmission rate, the determination unit 235c determines that the light amount of the optical signal is attenuated due to connection abnormality and the like at the optical connecting portion and preserving the transmission quality is difficult. Actually, the determination unit 235c acquires the transmission rate of the optical signal based on the intensity of the electric signal output from the filter 35b.

First, a case of acquiring a transmission rate of an optical signal of the route R1 will be described. In this case, the control unit 236 causes the optical switch 228 to select the optical cable 27a and connect the optical cable to the optical cable 27. Then, the control unit 236 causes the optical switch 233 to select the optical cable 32a and connect the optical cable to the optical cable 32. The determination unit 235c acquires the transmission rate of the optical signal in the route R1 based on the intensity of the electric signal output from the filter 35b and intensity of an electric signal corresponding to the light amount of the optical signal output from the optical transmitter 25 of the endoscope 202. Subsequently, in the case of acquiring a transmission rate of an optical signal of the route R2, the control unit 236 causes the optical switch 228 to connect the optical cable 27b to the optical cable 27, and causes the optical switch 233 to connect the optical cable 32b to the optical cable 32, and the determination unit 235c acquires the transmission rate of the optical signal in the route R2 based on the intensity of the electric signal output from the filter 35b. Additionally, in the case of acquiring a transmission rate of an optical signal of the route R3, the control unit 236 causes the optical switch 228 to connect the optical cable 27c to the optical cable 27, and causes the optical switch 233 to connect the optical cable 32c to the optical cable 32, and the determination unit 235c acquires the transmission rate of the optical signal in the route R3 based on the intensity of the electric signal output from the filter 35b.

As a result, the transmission rates of the optical signals in the respective routes R1 to R3 are acquired as shown in Table T in FIG. 6, for example. Transmission route selection control by the control unit 236 in this case will be described. As illustrated in FIG. 6, the determination unit 235c determines that there is no abnormality in the optical connecting portions because the transmission rate is 100% in the route R1 and the transmission rate is 98% in the route R2 among the routes R1 to R3, and both transmission rates are higher than the threshold (e.g., 50%). In contrast, the determination unit 235c determines that there is connection abnormality in the optical connecting portion in the route R3 because the transmission rate is low like 30% which is significantly lower than the predetermined threshold of the transmission rate. Based on a determination result by the determination unit 235c, the control unit 236 selects the routes R1 and R2 having the high transmission rates in order to surely preserve transmission quality of the optical signal. Therefore, the control unit 236 causes the optical switch 228 to connect both of the optical cables 27a and 27b to the optical cable 27 and causes the optical switch 233 to connect both of the optical cables 32a and 32b to the optical cable 32, and performs endoscopic examination by using the routes R1 and R2. Needless to say, the control unit 236 may select a single route, and in the example of FIG. 6, the control unit may select the route R1 that has the highest transmission rate to perform endoscopic examination.

Thus, according to the second embodiment, the plurality of routes is provided and the optical switch is controlled, thereby respectively obtaining the light amount of the optical signal transmitted in each of the routes, and presence of abnormality at the optical connecting portion in the optical transmission line can be detected by comparing the light amount with the predetermined threshold. Furthermore, according to the second embodiment, since the optical signal is transmitted by selecting the route having little loss of the light amount based on the determination result of the determination unit 235c, an optical signal in which loss of the optical signal is minimized can be transmitted. Moreover, according to the second embodiment, even in the event of connection abnormality due to dirt and the like at a part of the optical connecting portion, transmission processing of the optical signal can be continued by selecting a normal route having no connection abnormality although user does not perform cleaning for an optical connecting surface. Therefore, it is possible to reduce burden of cleaning by the user.

In the second embodiment, same as the first embodiment, the abnormality detection unit 235 performs abnormality detection processing for the respective routes R1 to R3 in pre-operation inspection under the control of the control unit 236, and the endoscope 202 can be started to be used in a state that reliability of optical transmission is secured by selecting the route in which no abnormality is recognized. Needless to say, in the endoscope system 201, the abnormality detection processing by the abnormality detection unit 235 can also be executed during still image generating operation by pressing a release button in the middle of endoscopic examination. There may be a case where angle deviation occurs at an optical connecting portion after pre-operation inspection, but in this case also, the control unit 236 controls the optical switches 228 and 233 to switch to the route having the highest transmission rate based on an abnormality detection result for each of the routes R1 to R3 by the abnormality detection unit 235 during examination. Consequently, normal transmission processing of the optical signal can be continued.

Because the dividing unit 28 and the optical switch 228 are provided to divide an optical signal and to select an optical cable, respectively, they are not necessarily provided at the connectors 23a and 223a, respectively, like FIG. 2 and FIG. 5 as long as they are provided at input stages of the optical connecting portions 29a to 29c. Because the coupling unit 33 and the optical switch 233 are provided to couple optical signals and to select an optical cable, respectively, they are not necessarily provided at the connectors 30 and 230, respectively, like FIG. 2 and FIG. 5 as long as they are provided at output stages of the optical connecting portions 31a to 31c.

Furthermore, in the first and second embodiments, examples of the endoscope systems 1 and 201 for medical use have been described, but needless to say, not limited to the medical use, application to an endoscope system for industrial use may also be possible and furthermore, not limited to the endoscope system, application to a detachable medical instrument may also be possible.

Third Embodiment

Figure 7:
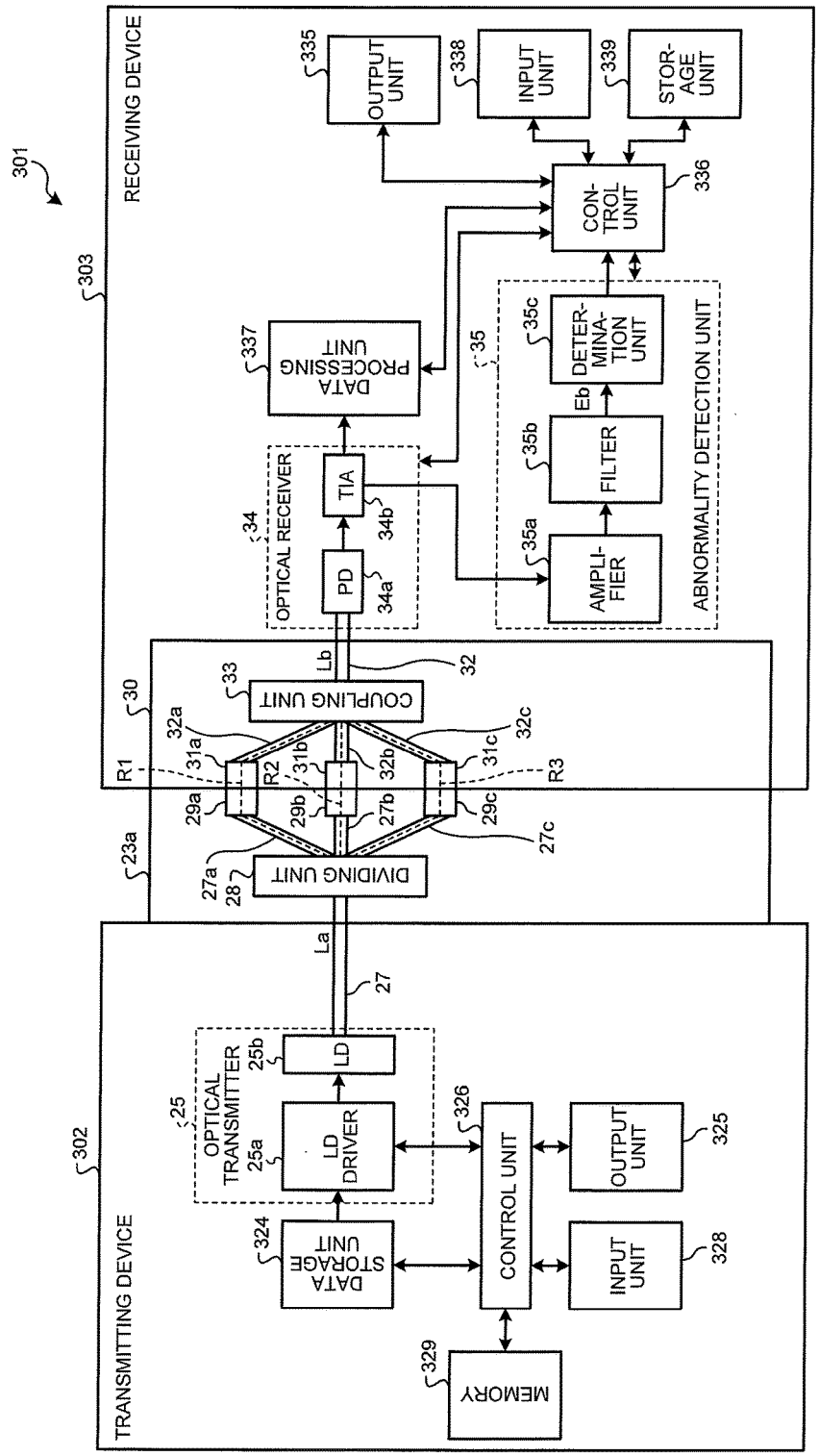
FIG. 7 is a block diagram schematically illustrating a configuration of an optical communication system according to a third embodiment.

Next, a third embodiment will be described. In the third embodiment, an example of applying a first embodiment to an optical communication system will be described. FIG. 7 is a block diagram schematically illustrating a configuration of an optical communication system according to the third embodiment.

As illustrated in FIG. 7, an optical communication system 301 according to the third embodiment includes: a transmitting device 302 adapted to transmit an optical signal; and a receiving device 303 adapted to receive the optical signal transmitted from the transmitting device 302. A connector 23a of the transmitting device 302 is removably connectable to a connector 30 of the receiving device 303. Thus the transmitting device 302 is attachable to and detachable from the receiving device 303.

The transmitting device 302 includes: a data storage unit 324 adapted to store information to be transmitted; an optical transmitter 25; an optical cable 27; the connector 23a; an output unit 325 adapted to output various kinds of information related to transmission processing and the like of the transmitting device 302; a control unit 326 adapted to control processing operation of each unit of the transmitting device 302; an input unit 328 adapted to receive input of various kinds of command information of the transmitting device 302; and a memory 329 adapted to store various kinds of programs in order to operate the transmitting device 302.

The receiving device 303 includes: the connector 30; an optical receiver 34; an abnormality detection unit 35; an output unit 335 adapted to output various kinds of information such as data received by the receiving device 303 and a detection result by the abnormality detection unit 35; a control unit 336 adapted to control processing operation of each unit of the receiving device 303; a data processing unit 337 adapted to process received data; an input unit 338 adapted to receive input of various kinds of command information of the receiving device 303; and a storage unit 339 adapted to store various kinds of data such as various kinds of programs in order to operate the receiving device 303 and the received data.

In order to detect presence of abnormality in a connection state between optical connecting portions 29a to 29c and optical connecting portions 31a to 31c same as the first embodiment, the abnormality detection unit 35 also automatically detects presence of abnormality in the connection state between the optical connecting portions 29a to 29c and the optical connecting portions 31a to 31c in the optical communication system 301 of the third embodiment as well, and transmission failure of an optical signal can be solved in an early stage same as the first embodiment.

Figure 8:
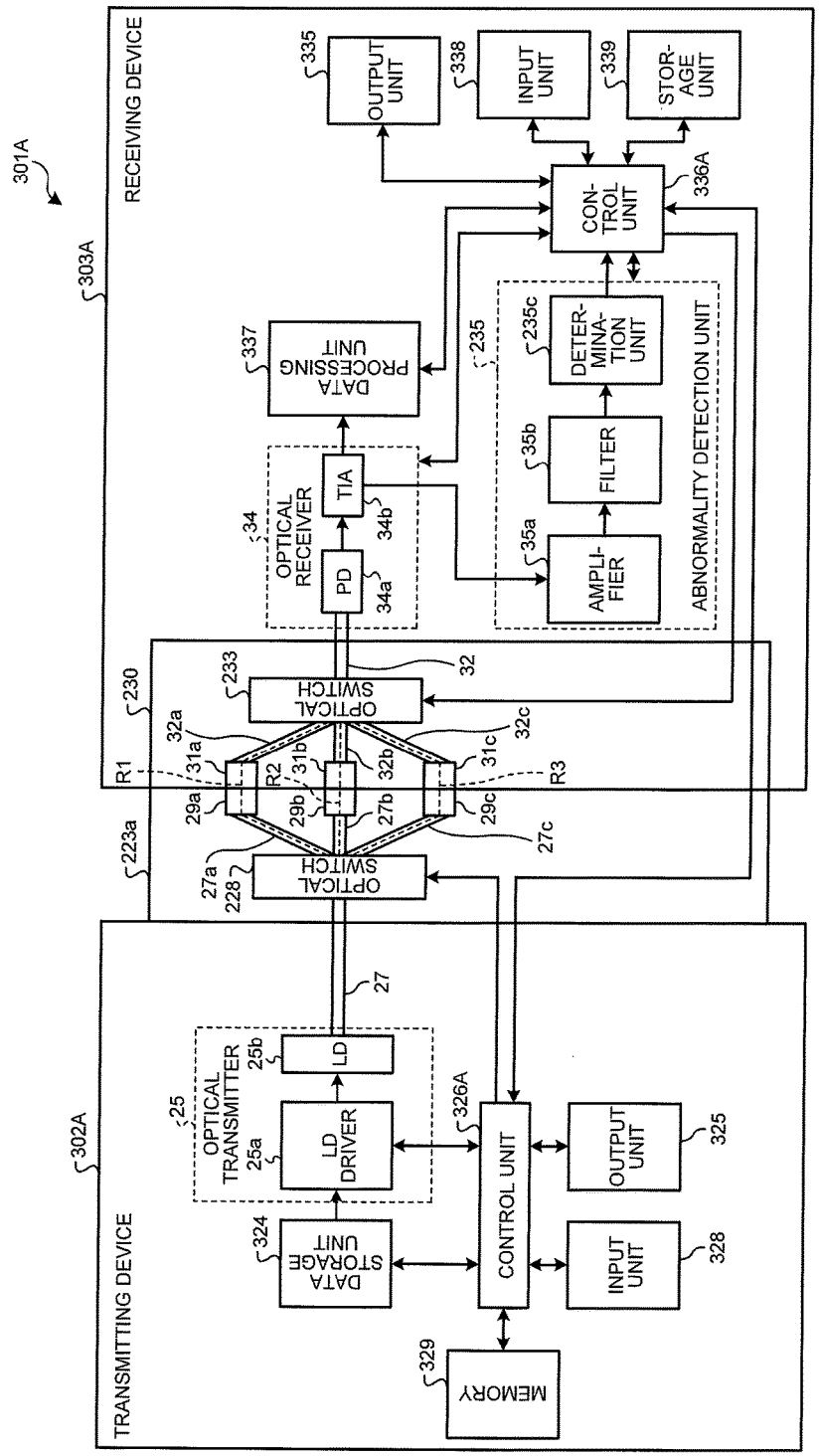
FIG. 8 is a block diagram schematically illustrating another configuration of the optical communication system according to the third embodiment.

Needless to say, a second embodiment may also be applied to the optical communication system. FIG. 8 is a block diagram schematically illustrating another configuration of the optical communication system according to the third embodiment. In an optical communication system 301A illustrated in FIG. 8, a transmitting device 302A includes a connector 223a instead of the connector 23a. An optical switch 228 of the connector 223a is controlled by a control unit 326A. Furthermore, a receiving device 303A includes a connector 230 and an abnormality detection unit 235 instead of the connector 30 and the abnormality detection unit 35. An optical switch 233 of the connector 230 is controlled by a control unit 336A. In this optical communication system 301A also, a transmission rate of an optical signal transmitted in each of routes R1 to R3 is obtained by controlling the optical switches 228 and 233 same as the second embodiment, and effects same as the second embodiment can be obtained by selecting a route having little loss of a light amount and transmitting an optical signal.

Other Embodiments

Figure 9:
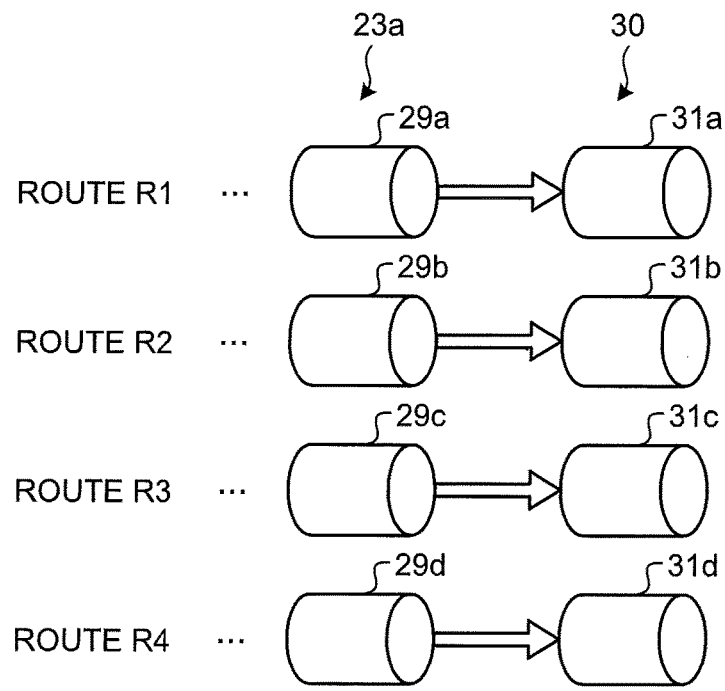
FIG. 9 is a diagram illustrating a different example of a light connecting portion on a transmitting side and a light connecting portion on a receiving side according to other embodiments.

Although, in the first to third embodiments, the optical signals are transmitted via the three routes R1 to R3, the number of the routes is not limited to three as long as multiple routes are provided, and optical cables and optical connecting portions are provided depending on the number of the routes. As illustrated in FIG. 9, for example, optical signals can also be transmitted by a division system of four routes R1 to R4. In this case, an optical cable (not illustrated) extending from a dividing unit 28 and an optical connecting portion 29d at a proximal end of the optical cable may be added to a connector 23a, and an optical connecting portion 31d and an optical cable (not illustrated) having a distal end provided with the optical connecting portion 31d and having a proximal end connected to a coupling unit 33 may be added to a connector 30, corresponding to the route R4.

Figure 10:
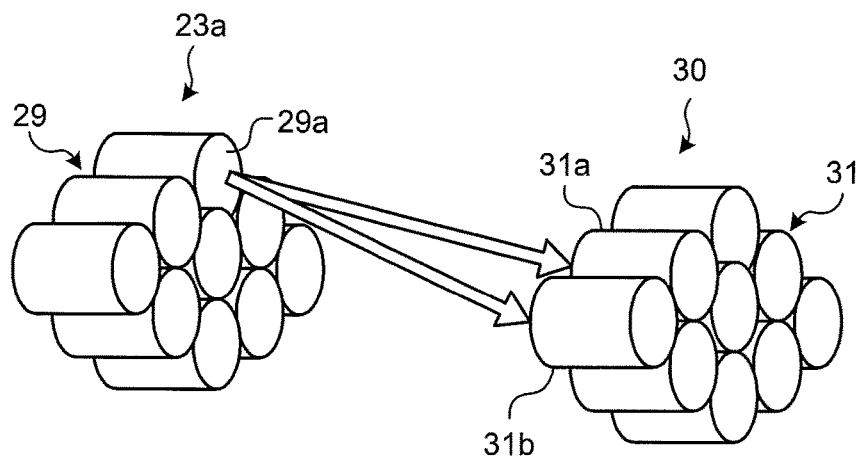
FIG. 10 is a diagram illustrating another different example of the light connecting portion on the transmitting side and the light connecting portion on the receiving side according to other embodiments.
Figure 11:
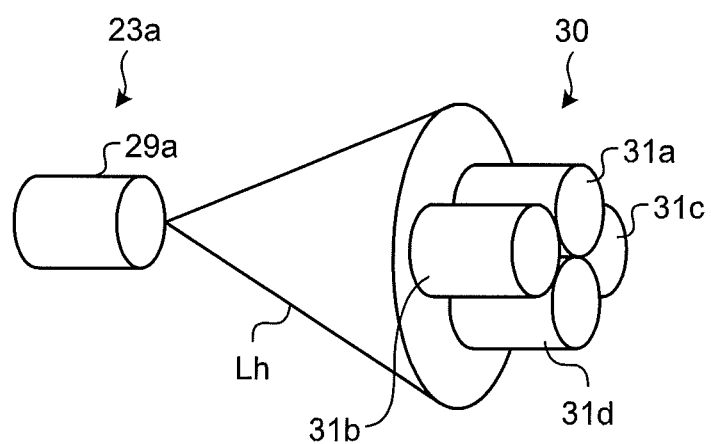
FIG. 11 is a diagram illustrating another different example of the light connecting portion on the transmitting side and the light connecting portion on the receiving side according to other embodiments.

Furthermore, in the first to third embodiments, the description has been given an example in which optical connecting portions 29a to 29d of the connector 23a on a transmitting side of an optical signal and optical connecting portions 31a to 31c of the connector 30 on a receiving side of the optical signal are provided on a one-to-one basis corresponding to the respective routes R1 to R3, but needless to say, not limited thereto. For example, as illustrated in FIG. 10, groups of optical connecting portions 29 and 31 formed of a plurality of optical connecting portions may be provided at the connector 23a on a transmitting side and a connector 30 on a receiving side respectively, and it may be possible to have a configuration in which an optical signal is received in the plurality of optical connecting portions 31a, 31b on the receiving side from the one optical connecting portion 29a on the transmitting side. Furthermore, as illustrated in FIG. 11, an enlarged light Lh is output from one optical connecting portion 29a on a transmitting side, and an optical signal can be received in four optical connecting portions 31a to 31d on a receiving side. Additionally, in the case where, only the optical connecting portion 29a out of four optical connecting portions 29a to 29d of the connector 23a on the transmitting side is normal and the three optical connecting portions 31b to 31d out of the four optical connecting portions 31a to 31d on the receiving side are normal, transmission of the optical signal may be compensated by delivering the optical signal from the optical connecting portion 29a to the three optical connecting portions 31b and 31d.

Furthermore, in the first to third embodiments, an example of notifying an operator of an abnormal connection state at an optical connecting portion by making a display device 5 display and output a warning menu and a caution menu has been described, but needless to say, not limited thereto. For example, a sound output device may be provided at each of the processing devices 3, 203, 303, and 303A, and sound information that indicates abnormality or possibility of abnormality at an optical connecting portion may also be output from the sound output device. Additionally, an LED lamp for abnormal notification or caution notification may be provided, and in the event of abnormality at an optical connecting portion, the lamp may be turned on or made to blink.

An execution program for each processing executed in the abnormality detection units 35 and 235 as well as other elements according to the present embodiments may be provided by being recorded in computer-readable storage media such as a CD-ROM, a flexible disk, a CD-R, and a DVD in an installable file form or an executable file form, and also may be provided by being stored on a computer connected to a network such as the internet and then be downloaded via the network. Additionally, the execution program may also be provided or distributed via a network such as the internet.

According to some embodiments, a transmitting side includes: a single first optical transmission unit; a second optical transmission unit having a plurality of optical transmission lines each having a proximal end at which a transmitting-side optical connecting portion is provided; and a dividing unit configured to divide an optical signal transmitted through the first optical transmission unit to produce divided optical signals and configured to deliver the divided optical signals to at least one of the optical transmission lines of the second optical transmission unit. A receiving side includes: a third optical transmission unit having a plurality of optical transmission lines each having a distal end at which a receiving-side optical connecting portion is provided, and configured to transmit the optical signal received from the receiving-side optical connecting portion; a coupling unit configured to couple the optical signals transmitted through the third optical transmission unit; a single fourth optical transmission unit configured to transmit the optical signal received from the coupling unit; and an abnormality detection unit configured to detect presence of abnormality in a connection state between the transmitting-side optical connecting portion and the receiving-side optical connecting portion based on light amount information of the optical signal transmitted through the fourth optical transmission unit. With this feature, it is possible to detect presence of abnormality at the connecting portion on the optical transmission line.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An optical communication system comprising:
a transmitter configured to transmit an optical signal; and
a receiver attachable to and detachable from the transmitter and configured to receive the optical signal transmitted from the transmitter,
the transmitter comprising:
a single first optical transmission line to receive the optical signal;
a plurality of second optical transmission lines each having a proximal end at which a transmitting-side optical connecting portion is provided; and
a first optical switch configured to select at least one optical transmission line from the plurality of second optical transmission lines, and to connect the at least one selected second optical transmission line to the single first optical transmission line, and
the receiver comprising:
a plurality of third optical transmission lines each having a distal end at which a receiving-side optical connecting portion is provided, the receiving-side optical connecting portion being optically connectable to the transmitting-side optical connecting portion, and the plurality of third optical transmission lines being configured to transmit the optical signal received from the receiving-side optical connecting portion;
a single fourth optical transmission line to transmit the optical signal;
a second optical switch configured to select, from the plurality of third optical transmission lines, an optical transmission line including the receiving-side optical connecting portion connected to the transmitting-side optical connecting portion of the at least one optical transmission line selected from the plurality of second optical transmission lines by the first optical switch, and to connect the selected optical transmission line to the single fourth optical transmission line; and
a controller comprising hardware, the controller being configured to:
control switching between the optical transmission lines connected to the first optical switch, and to control switching between the optical transmission lines connected to the second optical switch; and
detect whether or not a connection state between the transmitting-side optical connecting portion and the receiving-side optical connecting portion is abnormal based on light amount information of the optical signal transmitted through the single fourth optical transmission line by way of the optical transmission lines selected in accordance with switching control of the first optical switch and the second optical switch;
wherein the receiving device further comprises an electric signal conversion unit configured to convert the optical signal transmitted through the single fourth optical transmission line to an electric signal including the light amount information of the optical signal, and
the controller is further configured to detect whether or not the connection state between the transmitting-side optical connecting portion and the receiving-side optical connecting portion is abnormal based on the light amount information of the optical signal transmitted through the single fourth optical transmission line and included in the electric signal obtained through conversion by the electric signal conversion unit.

2. The optical communication system according to claim 1, wherein if a light amount of the optical signal transmitted through the single fourth optical transmission line is lower than a first light amount that is large enough to preserve a specific level of transmission quality of the optical signal, the controller is configured to detect that the connection state between the transmitting-side optical connecting portion of the at least one optical transmission line selected from the plurality of second optical transmission lines by the first optical switch and the receiving-side optical connecting portion of the optical transmission line selected from the plurality of third optical transmission lines by the second optical switch is abnormal.

3. The optical communication system according to claim 2, wherein if the light amount of the second optical signal transmitted through the single fourth optical transmission line is lower than a second light amount which is larger than the first light amount, the controller is configured to detect possibility that the connection state between the transmitting-side optical connecting portion of the at least one optical transmission line selected from the plurality of second optical transmission lines by the first optical switch and the receiving-side optical connecting portion of the optical transmission line selected from the plurality of third optical transmission lines by the second optical switch is abnormal.

4. The optical communication system according to claim 2, wherein the controller is configured to control the first optical switch to select the at least one optical transmission line from the plurality of second optical transmission lines, and to control the second optical switch to select the optical transmission line from the plurality of third optical transmission lines, correspondingly to the transmitting-side optical connecting portion and the receiving-side optical connecting portion in which no abnormal connection state is detected.

5. The optical communication system according to claim 1, wherein the controller is further configured to output a detection result.

6. An endoscope system comprising:
an endoscope configured to be inserted into a subject to image an inside of the subject; and
a processing device to and from which the endoscope is attachable and detachable,
the endoscope comprising:
an imaging sensor having a plurality of pixels arranged in a matrix form and configured to perform photoelectric conversion on light from an object irradiated with the light to generate an image signal;
an optical signal conversion unit configured to convert the image signal to an optical signal;
a single first optical transmission line to receive the optical signal;
a plurality of second optical transmission lines each having a proximal end at which a transmitting-side optical connecting portion is provided; and
a first optical switch configured to select at least one optical transmission line from the plurality of second optical transmission lines and to connect the at least one selected optical transmission line to the single first optical transmission line, and the processing device comprising:
a plurality of third optical transmission lines each having a distal end at which a receiving-side optical connecting portion is provided, the receiving-side optical connecting portion being optically connectable to the transmitting-side optical connecting portion, and the plurality of third optical transmission lines being configured to transmit the optical signal received from the receiving-side optical connecting portion;
a single fourth optical transmission line;
a second optical switch configured to select, from the plurality of third optical transmission lines, an optical transmission line including the receiving-side optical connecting portion connected to the transmitting-side optical connecting portion of the at least one optical transmission line selected from the plurality of second optical transmission lines by the first optical switch, and to connect the selected optical transmission line to the single fourth optical transmission line; and
a controller comprising hardware, the controller being configured to:
control switching between the optical transmission lines connected to the first optical switch, and to control switching between the optical transmission lines connected to the second optical switch;
detect whether or not a connection state between the transmitting-side optical connecting portion and the receiving-side optical connecting portion is abnormal based on light amount information of the optical signal transmitted through the single fourth optical transmission line by way of the optical transmission lines selected in accordance with switching control of the first optical switch and the second optical switch; and
process the image signal based on the optical signal transmitted through the single fourth optical transmission line;
wherein the processing device further comprises an electric signal conversion unit configured to convert the optical signal transmitted through the single fourth optical transmission line to an electric signal including the light amount information of the optical signal, and
the controller is further configured to detect whether or not the connection state between the transmitting-side optical connecting portion and the receiving-side optical connecting portion is abnormal based on the light amount information of the optical signal transmitted through the single fourth optical transmission line and included in the electric signal obtained through conversion by the electric signal conversion unit.

* * * * *